US008802641B2

(12) United States Patent
Koide et al.

(10) Patent No.: US 8,802,641 B2
(45) Date of Patent: Aug. 12, 2014

(54) METHOD FOR INHIBITING ONSET OF OR TREATING POLLEN ALLERGY

(75) Inventors: Masafumi Koide, Nagoya (JP); Ryutaro Tsuda, Nagoya (JP); Kenji Fujisawa, Motosu (JP)

(73) Assignee: Natura Corporation, Tokyo (JP)

( * ) Notice: Subject to any disclaimer, the term of this patent is extended or adjusted under 35 U.S.C. 154(b) by 1014 days.

(21) Appl. No.: 12/422,543

(22) Filed: Apr. 13, 2009

(65) Prior Publication Data
US 2009/0202601 A1  Aug. 13, 2009

Related U.S. Application Data

(62) Division of application No. 10/556,941, filed as application No. PCT/JP2004/006992 on May 17, 2004, now abandoned.

(30) Foreign Application Priority Data

May 16, 2003  (JP) ................................. 2003-139380

(51) Int. Cl.
A61K 48/00 (2006.01)
A61K 31/715 (2006.01)
A01N 43/04 (2006.01)

(52) U.S. Cl.
USPC ......................................... 514/44 R; 514/54

(58) Field of Classification Search
None
See application file for complete search history.

(56) References Cited

U.S. PATENT DOCUMENTS

| 5,310,548 | A |   | 5/1994  | Tsuru et al. |
| 5,869,457 | A |   | 2/1999  | Jansen et al. |
| 5,888,984 | A | * | 3/1999  | Brown ............................ 514/54 |
| 6,143,354 | A | * | 11/2000 | Koulik et al. ................ 427/2.24 |
| 6,320,030 | B1 |  | 11/2001 | Shukla et al. |
| 6,420,342 | B1 |  | 7/2002  | Hageman et al. |
| 6,598,699 | B2 |  | 7/2003  | Takehara et al. |
| 6,747,014 | B2 |  | 6/2004  | Teng et al. |
| 6,958,325 | B2 | * | 10/2005 | Domb ............................. 514/54 |
| 2005/0025846 | A1 | * | 2/2005 | Brown et al. ................. 424/742 |
| 2006/0293263 | A1 | * | 12/2006 | Koide et al. ..................... 514/44 |
| 2008/0191144 | A1 | * | 8/2008  | Bhatt et al. ............. 250/396 ML |
| 2009/0202601 | A1 | * | 8/2009  | Koide et al. .................. 424/402 |

FOREIGN PATENT DOCUMENTS

| EP | 0 497 341 | 8/1992 |
| EP | 01119429.7 | 8/2001 |
| JP | 04-090762 | 3/1992 |
| JP | 06-116152 | 4/1994 |
| JP | 6-505264 | 6/1994 |
| JP | 7-330617 | 12/1995 |
| JP | 7-330716 | 12/1995 |
| JP | 08-099860 | 4/1996 |
| JP | 2000-4881 | 1/2000 |
| JP | 2000-262247 | 9/2000 |
| JP | 2001-064895 | 3/2001 |
| JP | 2001-081098 | 3/2001 |
| JP | 2001-131074 | 5/2001 |
| JP | 2001-233777 | 8/2001 |
| JP | 2001-520181 | 10/2001 |
| JP | 2004-59440 | 2/2004 |
| WO | WO 95/26735 | 10/1995 |
| WO | WO 97/47194 | 12/1997 |
| WO | WO 98/17320 | 4/1998 |
| WO | WO 98/48626 | 11/1998 |
| WO | WO 00/25723 | 5/2000 |
| WO | WO 01/36656 | 5/2001 |
| WO | WO 01/47561 | 7/2001 |
| WO | WO 02/32406 | 4/2002 |

OTHER PUBLICATIONS

Database Medline [Online] US National Library of Medicine, Bethesda, Md. USA: Jan. 1997 Antczak-Marczak M et al., "[The influence of heparin on histamine level in plasma during the early reaction phase of asthma" XP002423806 & Polskie Archiwum Medycyny Wewn Trznej, Jan. 1997, vol. 97, No. 1, Jan. 1997. pp. 7-14.

Magone, M.T. et al., "Systemic or mucosal administration of immunostimulatory DNA inhibits early and late phases of murine allergic conjunctivitis", European Journal of Immunology, Weinheim, DE, vol. 30, No. 7, Jul. 2000, pp. 1841-1850, XP002206146.

Blumenkrantz, N. et al., "Reaction of Cationic Groups of Chlorpromazine with Anionic Macro Molecules: Complexes With DNA, RNA, Hyaluronic-Acid and Heparin", ACTA Pharmacologica et Toxicologica, Munksgaard, DK., vol. 34, No. 1, 1974, pp. 27-32, XP009080206.

Paponov et al. Bulletin of Experimental Biology and Medicine vol. 99 No. 3 Mar. 1985.

Higgins et al. Br. J. Ophthalmol 2006; (90:964-967).

Robert et al., The New England Journal of Medicine vol. 341: 1817-1828.

Definition of phegm.

Knekt et al. Eur J. Clin Nutr May 2000; 54(5):415-7.

Nickloff et al. J. Am. Acad Dermatol 2006: 54:S143-51.

Blam et al. The American Journal of Gastroenterology col. 96 No. 7 2001 p. 1977-1997.

Sigma Catalog 1995. p. 325 product No. D1501.

Sigma Catalog 1995 p. 775 product No. P2157, P9135.

Masanori Yamada et al., "UV-Irradiated DNA Matrixes Selectively bind Endocrine Disruptors with a Planar Structure", Environ. Sci. Technol. 2002, vol. 36, No. 5, 949-954.

Notice of Reasons for Rejection in corresponding Japanese Patent Application No. 2005-506285 and its English translation.

\* cited by examiner

Primary Examiner — Nita M Minnifield
(74) Attorney, Agent, or Firm — Young & Thompson

(57) ABSTRACT

The intermolecular mutual recognition between a disease-state inducing substance (e.g., allergen group, pathogen et cetera) and a living body which functions at the time when such a disease-state inducing substance reaches the living body is inhibited by making use of pectins and nucleic acids.

15 Claims, 3 Drawing Sheets

FIG. 3

Figure 1:
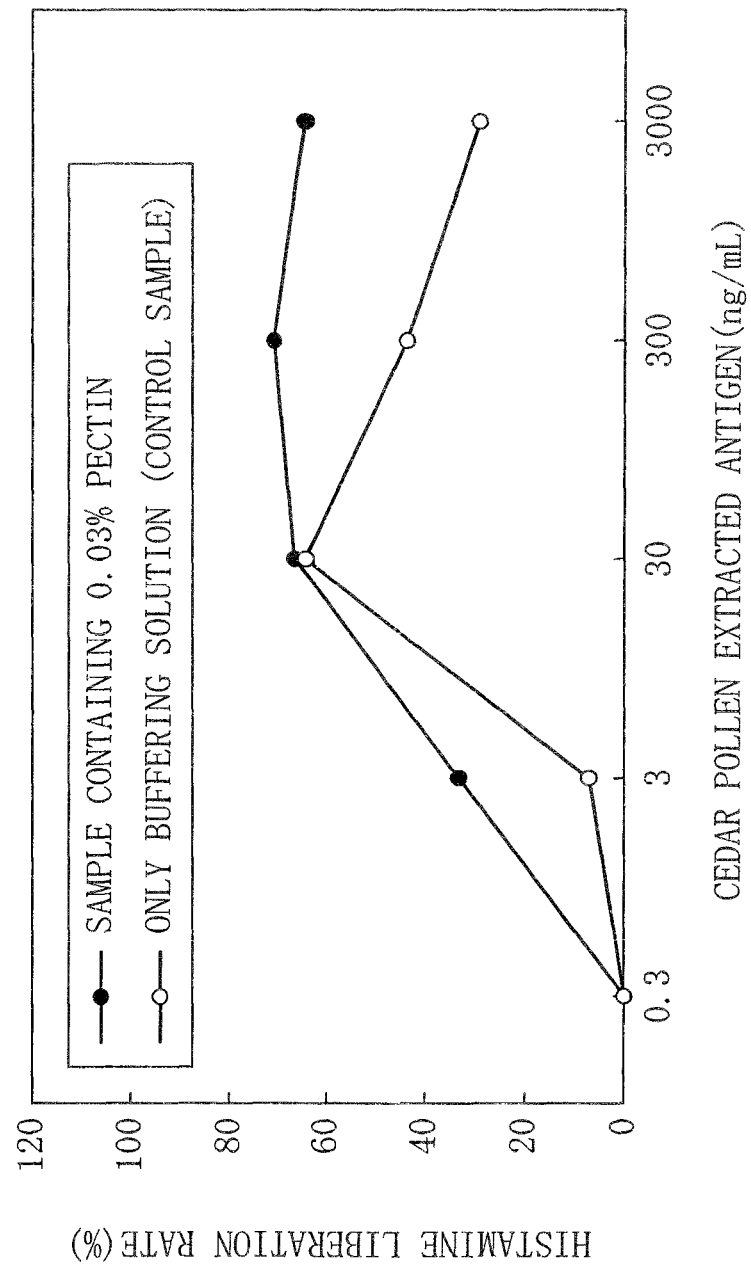
Figure 2:
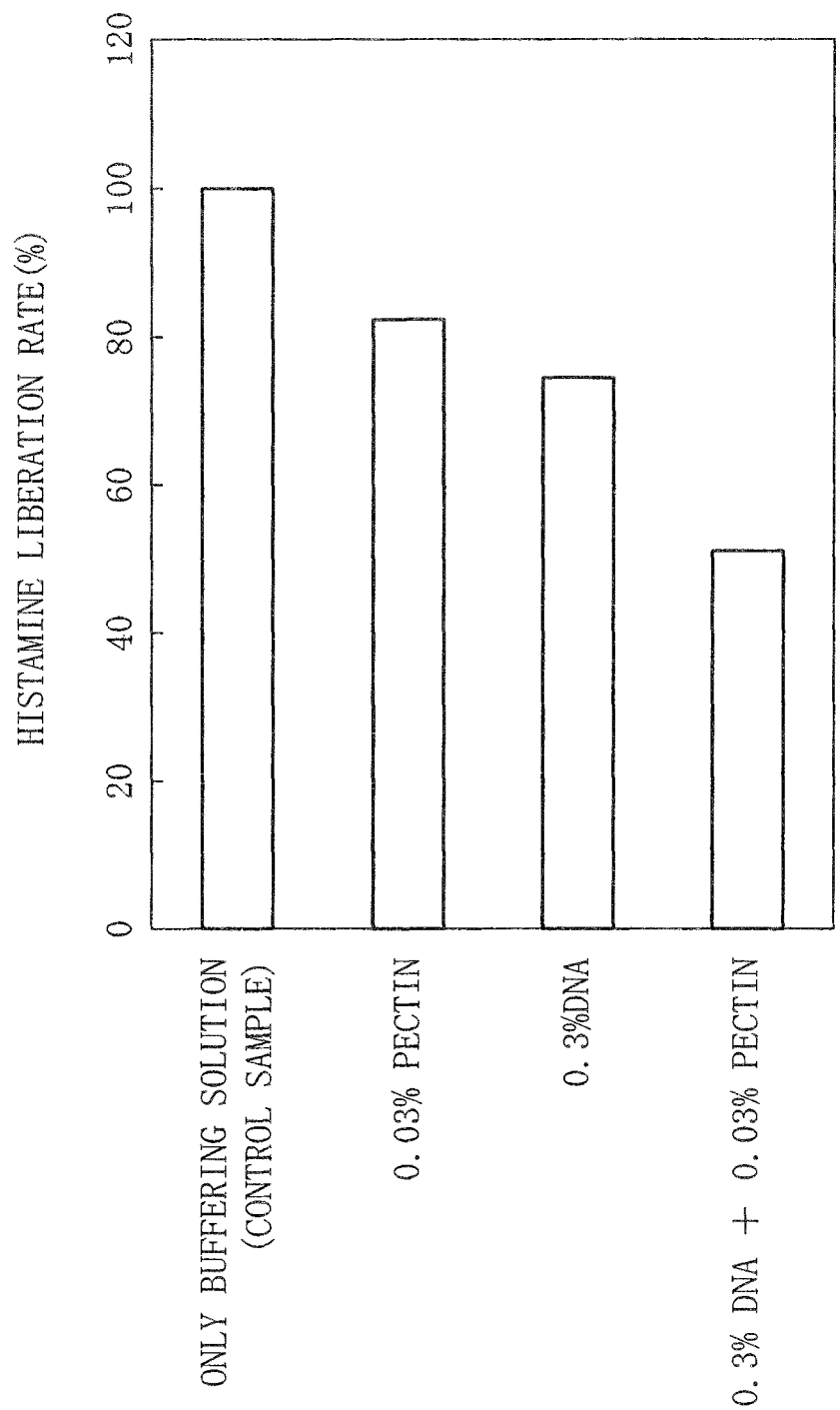

| BIOLOGICAL PREPARATION COMPONENTS | IMPROVEMENT IN ITCHING | DURATION | UNCOMFORTABLE FEELING | IMPROVEMENT AT GOING-OUT TIME | RESULT WHEN APPLIED AT BEDTIME | SNUFFLES ON AWAKENING |
|---|---|---|---|---|---|---|
| 0.5% PECTIN | AAA | AAA | A | AA | AA | AA |
| 0.5% DNA | AA | A | AA | AA | A | A |
| 0.5% PECTIN + 0.5% DNA | AAA | AAA | AA | AAA | AAA | AAA |
| 0.8% PECTIN + 0.2% DNA | AAA | AAA | A | AAA | AAA | AAA |
| 0.2% PECTIN + 0.8% DNA | AAA | AA | AA | AAA | AAA | AAA |
| SALINE | BB | BB | AA | BB | BB | BB |

METHOD FOR INHIBITING ONSET OF OR TREATING POLLEN ALLERGY

This application is a divisional of application Ser. No. 10/556,941 filed Nov. 16, 2005, now abandoned, which is a National Phase of PCT/JP2004/006992 filed May 17, 2004, which claims the priority of Japanese Application No. 2003-139380 filed May 16, 2003.

TECHNICAL FIELD

The present invention relates mainly to the reducing and mildening of exposure of the living body to exogenous disturbing factors in everyday life, to the provision of guarding means against infectious pathogens, and to preventing the progression of disease states. In particular, the basic technique of the present invention is to reduce the chance of establishment of bonding between a foreign substance and a living cell by the use of a third-party substance, thereby preventing a foreign disease-state inducing substance from making contact with a living-body surface area. More specifically, the present invention relates to a technique capable of inhibiting various allergens (which are substances triggering allergic reactions such as asthma, rhinitis, hives, food/pollen allergy, atopic dermatitis et cetera) and various pathogenic microbes (such as viruses and bacteria) from recognizing acceptors on the living-body side, thereby preventing or reducing the contact of the living body with such allergens and the invasion of the living body by such allergens. The present invention further relates to a curative biological preparation at the topical mucous or skin region fro mucous or skin inflammatory diseases.

BACKGROUND ART

Allergic reactions and inflammation caused by infectious diseases are examples of vital-function disorders caused by foreign disease-state inducing substances. Although these allergic reactions and inflammation are short-term symptoms in some cases, they may give rise to mid- and long-term unwelcome vital reactions. Especially, if such a symptom unfortunately continues over a long period of time, the inflammatory reaction will not come to an end but become prolonged, even after the disappearance of a disease-state inducing substance itself. This often produces troubles in the sufferer's daily life.

Especially, for the case of epidemic disease-states occurring seasonally explosively such as cedar pollen allergy and influenza, in order to avoid affection and sideration it is required not to be outdoors as far as possible. In addition, it is required to reduce the chance of being contact with disease-state inducing substances or with pathogens by providing a covering over part of the living body. However, it is inevitable that disease-state inducing substances which are invisible to the naked eye accidentally contact with a body surface or enter the living body. Therefore, the life of a person compromised to infection or vulnerable to allergens is seriously constrained.

In the past, such disease-state inducing substances have been dealt with by precautions (mask, gargling et cetera), by various symptomatic therapies, and by anti-inflammatory treatments, including various antibiotic substances, antiviral drugs, vaccines et cetera.

For example, as a way of coping with the cedar pollen allergy, medical treatments by desensitization using an anti-histamic agent, steroid, or vaccine have been carried out commonly. However, it is difficult for these treatments to work wonders. Besides, this kind of treatment may involve unignorable serious side effects in some cases. Consequently, in recent years natural substances have drawn attention as substances having few side effects and providing advantageous effects of suppressing allergic reactions.

More specifically, with respect to allergic reactions, human intervention research work on the allergy prevention effects by making use of apple pectin has been carried out by National Institute of Fruit Tree Science. The results have been reported, which show that the concentration of histamine in the blood after the ingestion of apple pectin drops by 24% in comparison with the concentration of histamine in the blood before ingestion.

Likewise, as a measure to deal with allergic diseases, there have been disclosed inhibition effects for the emission of cytokines by administration of pectin (see for example Japanese Patent Application Kokai Publication No. 2001-233777 which is hereinafter referred to as "Patent Document I"). With respect to the allergic reaction inhibition effect as set forth in the Patent Document I, the point of effect is a drop in the monocyto/macrophage reactivity owing to the administration of pectin. Stated another way, the pectin administration of the Patent Document I has a certain effect on the production inhibition of IL-5 (interleukin-5), on the production inhibition of IL-4 (interleukin-4), and on the production enhancement of IFN-gamma by altering cellular reactivity.

In addition, pectins have been used for the purpose of achieving stable dispersion/distribution and of the wetting of substances present in a solution. More specifically, pectins are added to various types of beverages and biological preparations as a stabilization agent (see for example Japanese Patent Application Kokai Publication No. 2001-64895 which is hereinafter referred to as "Patent Document II"). In the Patent Document II, a pectin is added to an eyedrop biological preparation and actions on the durability of beneficial effects of the eyedrop biological preparation are discussed. This method is one that also extends the residence time of a biological preparation in a local part through wetting distribution.

In addition, with respect to infectious diseases such as influenza, precautions by vaccines and the like, drug treatments as typified by amantadine, gargling, and avoidance of contact with viruses by wearing a mask are coping ways. As a curative medicine for influenza, a neuraminidase inhibitor has been disclosed (see for example JP 2000-505088 A (Japanese Translation of PCT International Application) which is hereinafter referred to as "Patent Document III). A biological preparation disclosed in the Patent Document III blocks an enzyme which takes partial charge of the function of cleaving a sialic acid present on the surface of a virus, thereby preventing the emitting of virus particles from a living cell surface.

Finally, it is reported that a sialyllactose-containing macromolecule exhibits a strong inhibition activity against type H1 influenza virus HA. Furthermore, it is reported that a macromolecule, combined with sialic acid monosaccharide as C- or S-glycoside, exhibits a strong inhibition activity against type H3 influenza virus HA. In addition, a medicine has been disclosed which contains as an active ingredient a chemical compound which is a low molecular weight sialic acid derivative and which exhibits an inhibition effect on two kinds of membrane proteins, i.e., sialidase and hemagglutinin (see for example Japanese Patent Application Kokai Publication No. 2001-131074 which is hereinafter referred to as "Patent Document IV).

Problems to be Solved

However, there are the following problems with the above-described conventional methods.

More specifically, the aforesaid conventional allergic-reaction improvements with the aid of pectin is unable to inhibit the manifestation of allergic reactions of the immediate type, because supportive effects are obtainable only by regular ingestion of pectin and an action mechanism is also through the reduction in cytophysiological response to allergen irritation.

Furthermore, the prevention method by inoculation with vaccine requires a certain period of time (from the time of vaccination to the time that a defense mechanism is built). In addition, depending upon the type of disease-state inducing substance, vaccination should be inoculated more than once. Consequently, in some cases, allergic reactions or inflammation will have developed before the manifestation of effects by vaccination, and it has been reported that there are cases where the vaccination fails to provide curative effects.

Additionally, the effects of dealing with disease states by administration of the foregoing medical agents are limited, and in most cases it takes considerable periods of time to recover from inflammation and other disease.

In view of the drawbacks described above, complete blocking of the entrance of disease-state inducing substances into the living body or deactivation of the pathological activity of disease-state inducing substances at the time of entrance into the living body can be regarded as preferable protective methods against allergen, virus and so on.

Consequently, the inventors of the present invention aimed at establishing, against allergen groups or pathogenic organisms (viruses), a new intermolecular mutual action between such a disease-state inducing substance and a living body, with a view to preventing or reducing contact therebetween.

DISCLOSURE OF INVENTION

The inventors of the present invention, focusing their attention on the physical property, stereo structure, physiochemical function of disease-state inducing substances including allergen groups such as Cry j1 and Cry j2 which are cedar pollen allergens and pathogens such as influenza pathogens, proposed a scheme to prevent establishment of contact between such a disease-state inducing substance and a living body.

For example, polysaccharide present on the surface of a cell functions as a point of contact and is connected to the cell as a glycoprotein's sugar chain component on the cell surface. In these glycoproteins connected to the cell, mucopolysaccharide present in mucin and uronic acid are component substances. Here, structural resemblances are stored in the polysaccharide connected to the cell surface and the freely-distributed uronic acid-containing polysaccharide or mucopolysaccharide. In other words, by making utilization of the existence of physical-property resembling regions in the uronic acid-containing polysaccharide, mucopolysaccharide, and mucin-containing glycoprotein which are all giant molecules, it is possible to completely separate a disease-state inducing substance from a living body by intercalation of a freely-distributed uronic acid-containing polysaccharide, mucopolysaccharide, or glycoprotein such as mucin between the disease-state inducing substance and the living body. Especially, it is expected that sufficient proximity of part of a region defined between polysaccharides which are giant molecules or between glycoproteins results in the enclosing of a disease-state inducing substance by most of the region.

Of the disease-state inducing substances, an influenza virus is comprised of a membrane envelop made up of two types of surface spike proteins having an interaction with sialyloligosaccharide present on a host cell (red blood cell). These surface spike proteins are called hemagglutinin and neuraminidase (sialidase), respectively. It is known that hemagglutinin bonds to a host-cell structure containing sialic acid, galactose, and N-acetylglucosamine. In the present invention, focusing attention on the bonding manner of enzyme to substrate, contact between a pathogen such as influenza virus and a living body is inhibited by making utilization of the specific or nonspecific competitive bonding relationship of the substrate and its analogous molecule with respect to the saccharide and protease.

In addition, generally most of the disease-state inducing substances such as various allergens and viruses are charged positive at their surface, therefore having such a property that they are liable to adhere to a negatively-charged cell surface. Focusing attention also on the physical properties of disease-state inducing substances described above, the present invention was made. More specifically, the disease-state inducing substance is drawn in by making use of a negatively-charged substance and the surface of the disease-state inducing substance is blocked, thereby preventing the disease-state inducing substance from adhering to the cell.

Based on the foregoing matters, a substance that exhibits a physical property capable of preventing a disease-state inducing substance from making contact with a living body surface is designed and formed in the present invention. The development of diseases caused by disease-state inducing substances is prevented and the mildening of disease states is achieved.

In the next place, supposedly a partial region of the polysaccharide which exhibits a variety of stereo structures and which is charged negative should be distributed in proximity to virus particles having a structure in which nucleic acid is coated with an envelope or to various types of positively-charged allergens. Furthermore, nucleic acid and a group of amino acid molecules which are charged negative exhibit the property of attracting a positively-charged allergen or virus particle in a micro space. In addition, it is preferable to contain a substance that provides a condition of making it difficult for various molecular complexes to be connected and agglutinated, i.e., a substance having a dispersion activity.

In addition, the present invention includes, as a curative biological preparation for endogenous factors, one for mucous membrane inflammatory diseases that contains therein either uronic acid-containing polysaccharide or nucleic acid.

Effects of Invention

In accordance with the present invention, it is possible to prevent contact of various types of exogenous disease-state inducing substances with a living body or with a cell surface. This therefore makes it possible to prevent the manifestation of diseases states of allergosis and infectious diseases and to improve symptoms of these diseases. For example, for the case of pectin-containing contact preventive biological preparations of the present invention, pectin functions as a substrate with respect to an enzyme which is a pollenosis inducing allergen, thereby preventing contact of pollen with a living body. On the other hand, for the case of nucleic acid-containing contact preventive biological preparations of the present invention, nucleic acid molecules having strong negative charges enclose the surface of pollen (virus et cetera) having positive charges, thereby preventing contact of the pollen with a living body.

Finally, in accordance with a thirtieth invention, various types of endogenous inflammation related components are taken into a stereo structure or masked from a mucous membrane and inflammatory cell, thereby making it possible to get rid of inflammation around the mucous membrane or to help it to be in remission.

BRIEF DESCRIPTION OF DRAWINGS

FIG. 1 is a diagram graphically representing a relationship between the concentration of cedar pollen extracted antigen and the rate of liberation of histamine;

FIG. 2 is a diagram graphically representing a multiplicative relation of pectin and DNA with respect to the histamine liberation rate suppressing effect; and FIG. 3 is a diagram showing test results of the application of an eyedrop biological preparation according to the present invention.

BEST MODE FOR CARRYING OUT INVENTION

Hereinbelow, embodiments of the present invention will be described in detail.

Embodiment 1

A contact preventive biological preparation according to a first embodiment of the present invention for preventing contact of a disease-state inducing substance with a living body contains pectin. Alternatively, the contact preventive biological preparation of the present embodiment contains at least either a pectin-analogous uronic acid-containing polysaccharide which is a uronic acid-containing polysaccharide or pectin-derived substance which is a substance derived from the uronic acid-containing polysaccharide.

Pectin, which is one of a group of polysaccharides constituting a plant cell wall, is a substance which contains a large amount of polygalacturonan which is a combination of galacturonic acids and which further contains, as a main chain, a small amount of rhamnogalacturonan which is an alternating combination of rhamnose and galacturonic acid, wherein any one of arabinose, xylose, fucose, rhamnose, and galactose or more than one of them are bonded, in a comb fashion, to a rhamnose residue of the rhamnogalacturonan as a side chain.

In addition, the aforesaid pectin-analogous uronic acid-containing polysaccharide includes alginic acid abundant in seaweeds, and dermatan sulfate, chondroitin sulfate, chondroitin, hyaluronic acid, heparin et cetera occurring abundantly in animal's skin, cartilage, internal organs et cetera. In the respective uronic acid-containing polysaccharides, pectin has a galacturonic acid; alginic acid has a mannuronic acid and guluronic acid; hyaluronic acid has a glucuronic acid; dermatan sulfate has an iduronic acid; chondroitin sulfate has a glucuronic acid; and heparin has a glucuronic acid and iduronic acid, as their main constitutive uronic acid.

In addition, the aforesaid pectin-derived substance is one that is obtained by subjecting pectin to heating, application of pressure, or oxidization or by chemical modification of pectin, for improvements in pectin physical property.

Pectin occurs in fruits. For example, apples in the dried state contain approximately a bit less than 10% pectin by weight. On the other hand, brown seaweeds such as kelp in the dried state contain approximately 20% alginic acid. Hyaluronic acid, which is a pectin-analogous uronic acid-containing polysaccharide, occurs in umbilical cord and cock's comb. Dermatan sulfate occurs in skin, tendon, internal organs et cetera. Chondroitin sulfate occurs in shark's cartilage (from 20 to 40% by weight in the dried state) and skin. Heparin occurs in internal organs and so on. Additionally, uronic acids (e.g., glucuronic acid, galacturonic acid, mannuronic acid, iduronic acid, guluronic acid et cetera) have a structure having a carboxylic group formed by oxidation of part (a sixth alcohol group) of the chemical structure of monosaccharide (e.g., such as glucose, galactose, mannose, idose, gulose et cetera).

Mucopolysaccharide, which is an analogue of the uronic acid-containing polysaccharide, exists in animal's connective tissues and body fluids in the heteropolysaccharide and contains therein an amino acid. Mucopolysaccharide combines with a protein substance in a living body, and a complex of a mucopolysaccharide having a structure formed by disaccharide repetition and a protein substance is called a "proteoglycan". The proteoglycan includes mucin. Mucin is a main glycoprotein of the mucus with which internal cavities such as trachea, digestive tract such as gastrointestinal tract, gonad et cetera in the living body are covered. In addition, vegetables, such as okra, morohaiya, basellaceae (tsurumurasaki), angelica keiskei (ashitaba), aroid, nameko mushroom et cetera, contain mucin abundantly.

In the present invention, disease-state inducing substances include allergens such as cedar pollen and pathogenic microbes such as influenza viruses.

The main allergen of cedar pollen is a saccharide splitting enzyme that functions at pollen fertilization time. Supposedly, the saccharide splitting enzyme falls into two types, namely Cry j1 (molecular weight: approximately 45,000 daltons; isoelectric point: from 8.9 to 9.2) and Cry j2 (molecular weight: approximately 37,000 daltons; isoelectric point: 9.5 or greater). Accordingly, the blood serums of many cedar pollen allergy patients recognize Cyr j1 and Cry j2 as an allergen.

Pectin contained in the contact preventive biological preparation according to the present embodiment is an enzyme substrate which is digested and decomposed by Cry j1 which is a pectate lyase functioning at the time of pollen fertilization and Cry j2 which is a polymethyl galacturonase, and is a water-soluble polysaccharide. Furthermore, Cry j1 and Cry j2 are molecules that are highly homologous to saccharide splitting enzymes occurring in any other plants/vegetables. Accordingly, there occurs an enzyme versus substrate reaction between the pectin, pectin-analogous uronic acid-containing polysaccharide or pectin-derived substance and Cry j1 or Cry j2 present on the pollen surface. Furthermore, since the pectin substrate is a giant molecule, new substrate structures will be presented one after the other even when enzyme-digested.

Universally, with respect to a plurality of substrates, saccharide or protease recognizes a stereo structure similar thereto and performs its function by splitting a glucoside bond or an amino acid bond. Accordingly, pectin exhibits a property recognizable not only by Cry j1 and Cry j2 but also by proximate saccharide splitting enzymes of pollen origin.

Allergens can cause allergic reactions only by being recognized by antibodies. That is to say, in the case where a third-party molecule of some kind modifies the stereo structure of an allergen and bonding to the main body of the allergen is inhibited by antibody molecules, no allergic reaction is induced. The pectin contained in the contact preventive biological preparation according to the present embodiment is able to prevent allergic reactions from occurring suddenly by being present between pollen and immunoglobulin E (Ig E) of the hay fever sufferer. The interposition of pectin or its analogous substance between pollen and a living cell is an effective way for the prevention of pollen allergic reactions.

On the other hand, two types of spike proteins are found on the surface of an influenza virus which is a typical pathogenic microbe. Of these two different spike protein substances, hemagglutinin is a protein essential for viruses to bond to ganglioside and to a sialic acid-containing glycoprotein receptor present on a host-cell membrane, while on the other hand neuraminidase (sialidase) has a function of splitting sialic acid from a receptor on a cell membrane.

That is to say, influenza exerts infectious properties when hemagglutinin and neuraminidase (which are approaches of the influenza to a living cell) recognize a sialic residue of the glycoprotein. In addition, a coagulation factor 10 which is a protease on the host side and a bacterial protease play a decisive role in the splitting of hemagglutinin.

In addition, the activity of the factor 10 functioning here is inhibited by heparin which is a uronic acid. Because of this, a repeated sequence of galacturonic acid by pectin and a repeated sequence of glucuronic acid and iduronic acid by heparin are interposed between a virus and a living cell, thereby inhibiting them from bonding together.

In the manner as described above, pectin and uronic acid such as heparin are useful for preventing the occurrence of unwelcome vital reactions by inhibiting the approaching of a disease-state inducing substance to a living body.

In the contact preventive biological preparation of the present invention, in addition to the already described essential components, the following additives and any other agents having medicinal properties may be combined in the range of not interfering with the effects of the present invention. More specifically, they are all kinds of buffering agents usually used in the formation of biological preparations for external use, solubilizing agents, isotonizing agents, stabilizing agents, tackifying agents, chelating agents, pH adjusters, refrigerant agents, antimicrobial agents, antiinflammatory agents et cetera.

More specifically, for example, boric acid or its salts including borax, citric acid or its salts including sodium citrate, phosphoric acid or its salts including phosphoric acid-sodium hydride, tartaric acid or its salts including sodium tartrate, gluconic acid or its salts including sodium gluconate, acetic acid or its salts including sodium acetate, and various types of amino acids or a combination thereof, can be used as a buffering agent.

For example, polyethylene glycol, propylene glycol and so on can be used as a solubilizing agent.

Next, sodium chloride, potassium chloride, mannitol, propylene glycol and so on can be used as an isotonizing agent.

Edetate sodium, cyclodextrin, sulfite salt, citric acid or its salts can be used as a stabilizing agent.

Polyethylene glycol, polyvinyl alcohol, polyvinyl pyrrolidone, hydroxyethyl cellulose, hydroxypropyl methylcellulose, methylcellulose, chondroitin sulfate sodium can be used as a tackifying agent.

Edetate sodium, sodium citrate and so on can be used as a chelating agent.

Hydrochloric acid, citric acid or its salts, boric acid or its salts, phosphoric acid or its salts, acetic acid or its salts, tartaric acid or its salts, sodium hydroxide, potassium hydroxide, sodium carbonate, sodium hydrogen carbonate and so on can be used as a pH adjuster.

Menthol, borneol, camphor, geraniol, limonene, eugenol, mentha oil, eucalyptus oil and so on can be used as a refrigerant agent.

For example, steroid, decongestant (naphazoline hydrochloride, tetrahydrozoline hydrochloride, phenylephrine hydrochloride et cetera), antiflash and astringent agents (neostigmine methylsulfate, epsilon aminocaproic acid, allantoin, berberine chloride, zinc sulfate, lysozyme hydrochloride et cetera), antihistamic agents (diphenhydramine hydrochloride, isothipendyl hydrochloride, chlorpheniramine maleate et cetera), vitamins [vitamin A and its esters (for example, acetate ester and palmitate ester), activated vitamin B2, vitamin B6, vitamin B12, and vitamin E and its esters (for example, acetate ester et cetera)], amino acids (L-potassium aspartate, L-magnesium aspartate, aminoethylsulfonic acid, chondroitin sulfate sodium et cetera), sulfonamide, bactericide (sulfur, isopropyl methylphenol, hinokitiol et cetera), topical anesthetic (lidocaine, lidocaine hydrochloride, procaine hydrochloride, dibucaine hydrochloride et cetera), and other agents can be combined in the proper proportions with the contact preventive biological preparations of the present invention.

The ph of an external-use composition of the present invention is not limited to particular values as long as it falls within a biologically-acceptable range, generally within the range of from pH 4 to pH 10 (more preferably within the range of from pH 5 to pH 8.5). Although the dose of a composition for external application prepared in accordance with the present invention is not limited to particular amounts as long as it falls within a biologically-acceptable range, it is preferable that, when used as eyedrops or as nosedrops or when used as a spray, a dose to be taken at one time is from 50 to 200 μL and the frequency of administration is from four to six times a day.

Furthermore, in the contact preventive biological preparation of the present embodiment, in addition to the above-described pectin basic components, it is possible to add components of plant origin. The origin of pectins themselves is found in various types of plants. Separated products in various stages of a process such as hydrolysis of a plant component comprise a pectin as their active constituent and become a biological preparation that contains any other components of plant origin.

In general, components of plant origin are sorted to water soluble fiber, non water soluble fiber, protein, fat, and sugar and are classified to plant (vegetable) fiber, alkaloid, saponin, tannin, catechin, aponycine, amaroid, phlegm, glycoside, flavonoid, vitamin, organic acid, and mineral.

These plant-origin components have various functions including aromatic actions, natural bactericidal actions, carbohydrate surface activities, anti-inflammatory actions, hyaluronidase inhibiting actions, proteinization reaction inhibiting actions et cetera. By virtue of these advantageous actions, plant-origin components have been used widely in the fields of drugs and medicines, articles of toilet, foods et cetera.

Accordingly, the biological preparation of the present embodiment, whose active constituents are pectins, pectin-analogous uronic acid-containing polysaccharides (or pectin-derived substances), and the aforesaid various plant-origin components, exerts combined functions together with the pectins. Therefore, the biological preparation of the present embodiment proves useful to prevent the occurrence of unwelcome vital reactions including allergic reactions. In addition, in the biological preparations as set forth in claims of the present invention, it is possible to combine not only plant extracts but also conventional biological preparation additives including electrolytes and various types of medicated components with the biological preparations of the present invention.

The foregoing plant-origin components are found in various types of plants and are especially originated from Japanese cedars. Separated products in various stages of a treatment process (such as fragmentation and hydrolysis of a cedar component composed of tree-constituting portions such as young leave, branch, root, trunk, seedling, callus et cetera) become a biological preparation which comprises an active constituent including pectin. Tree portions which exhibit flexible and active functions (especially, callus, growing point, young tree) are preferable as a starting material.

Here, the compounding ratio of various components of cedar origin with respect to a pectin, pectin-analogous uronic acid-containing polysaccharide or pectin-derived substance can be set arbitrarily. In addition, a component, extracted as a pectin containing fractionation in a course of processing and sorting cedar components, may be used. Furthermore, it is preferred that, in addition to the essential components, various components used usually in manufacturing biological preparations for external application are added to the biological preparation of the present embodiment.

It may be arranged such that the contact preventive biological preparation according to the present embodiment contains at least any one of any other saccharide, a macromolecular compound, and a nonionic surface-active agent.

In the contact preventive biological preparation, at the time when developing a substance, such as pectin, pectin-analogous uronic acid-containing polysaccharide and derivative thereof, in a solvent, the substance is unevenly distributed in some cases because of a disease-state inducing substance and an ambient environment. As a result, the biological preparation becomes insufficient in penetration, emulsification, cleaning power, and refining power. In order to cope with this, addition of a macromolecular compound or a nonionic surface-active agent is effective.

As the macromolecular compound, for example, polyvinyl alcohol, polyvinyl pyrrolidone, hydroxyethyl cellulose, hydroxypropyl methylcellulose, methylcellulose, cyclodextrin et cetera may be used. On the other hand, as the nonionic surface-active agent, polyoxyethylene higher fatty acid ester, polyoxyethylene sorbitan higher fatty acid ester, glycerin fatty acid ester, sorbitan fatty acid ester, cane sugar fatty acid ester et cetera may be used. More specifically, for example, polyoxyethylene hardened ricinus, polyoxyethylene sorbitan monooleate et cetera may be used.

These compounds may be used alone or in the form of a proper combination of two or more of them. In addition, the use of a chelating agent is effective to prevent water insolubilization by Ca or Mg. Lipase is effective for the decomposition of oil and fat components.

In addition, when forming a molecular structure which easily expands between pectins by coexistence with a different saccharide (e.g., trehalose) capable of enhancing the property of development to a water solution, it is possible to safely improve the property of dispersion of the pectin. Because of this, it becomes possible to enhance the contact prevention effect of pectins, pectin-analogous uronic acid-containing polysaccharides, or derivatives thereof present in a solvent of the contact preventive biological preparation.

By the adding of the aforesaid macromolecular compound and nonionic surface-active agent, the biological preparation is improved in penetration, emulsification, cleaning power, and refining power to satisfactory levels. As the result of this, the contact preventive biological preparation is given improved latitude in the way of application as well as in the form of dosage.

When put in place around part of a living body, each of the aforesaid contact preventive biological preparations according to the present embodiment functions to effectively prevent contact of a disease-state inducing substance with the living body.

Here, the above-described contact preventive biological preparation application around the living body includes administration directly onto a surface area of the living body.

More specifically, the contact preventive biological preparations of the present embodiment are put in place around part of a living body in the following useful manners. That is, the contact preventive biological preparation is fixed to an attach means (e.g., mask, goggle, cap, clothes, air conditioner filter, tape) by an adequate technique, thereby being wearable by a sufferer. On the other hand, in the case where the contact preventive biological preparation is administered onto a living body surface, it is effective that the biological preparation is distributed around a local part of the living body surface to which allergens and pathogens are liable to adhere. In other words, direct administration of the contact preventive biological preparation to a mucous membrane which is wet, which is not covered with any clothes, and in which Ig E antibodies or sugar chains appear on a living body surface or to a skin area, is an effective way. In view of this, as an applicable form of dosage, biological preparations for external application, such as an eyedrop biological preparation, nosedrop biological preparation, eardrop biological preparation, inhalant biological preparation, gargling biological preparation, spray biological preparation, liniment biological preparation, medical application biological preparation, cleaning biological preparation, intestinal infusion biological preparation et cetera, are preferable.

Embodiment 2

A contact preventive biological preparation for preventing contact of a disease-state inducing substance with a living body according to a second embodiment of the present invention contains at least either a nucleic acid or derivative thereof. By this nucleic acid-derived substance here is meant either a substance as a result of a decomposition process of DNA or RNA or a substance as a result of improvement in nucleic acid physicality by application of a chemical modification.

In the present embodiment, nucleic acids are macromolecules which are charged negative. In the nucleic acids, DNA is a stable structure, while on the other hand RNA is a vulnerable structure responsible for a short-term function. It is known that these structures form, together with saccharide and protein, a complex and exert physiological functions. Furthermore, they are split or synthesized by an enzyme to change into a greater sequence. In addition, it is possible to mass-produce nucleic acids having a desired base sequence by multiplying nucleic acid-incorporated bacteria and cells.

In general, positively charged disease-state inducing substances, e.g., various types of allergens and viruses, are predisposed to come into contact with a negatively charged cell surface. On the other hand, the nucleic acid exhibits such a property that the nucleic acid and a positively charged molecule such as liposome attract each other. This is because there is held at least a negative charge per pentose of a biological molecule, and DNA and RNA each contain a negative charge per nucleotide. Stated another way, unlike ordinary micro molecules, the nucleic acid is an entirely heavily negatively charged macromolecule.

Accordingly, the nucleic acid and a disease-state inducing substance (e.g., a positively charged allergen or pathogenic microbe) strongly attract each other and, as a result, the nucleic acid adheres to the surface of the disease-state inducing substance. This causes the disease-state inducing substance to lose its charges, as a result of which the disease-state inducing substance is lowered in capability of adhering to a negatively charged cell surface and loses a point of contact with a specific receptor present on a living body surface. In addition, the fact that the nucleic acid is a macromolecule is an overwhelming advantage over other micro molecules in view of the point that it provides a covering all over a disease-state inducing substance.

To sum up, the contact preventive biological preparation of the present embodiment which contains either a nucleic acid or nucleic acid-derived substance exhibits functional properties of inhibiting the capability of bonding of a disease-state inducing substance to a living body surface before the former arrives at the later.

More specifically, nucleic acid is a water soluble heteropolysaccharide that forms a complex together with a saccharide, and a nucleotide unit is a chain macromolecule compound linked long by phosphodiester linkage. On the other hand, Cry j1 and Cry j2, which are saccharide splitting enzymes, have been known as allergens causing most cedar pollen allergies. Such allergens can cause allergic reactions only when recognized by antibodies, and if a nucleic acid which is a heteropolysaccharide or derivative thereof is coupled to an allergen, no allergic reactions will be induced because Ig E antibodies fail to recognize the main body of the allergen.

Accordingly, the nucleic acid of the contact preventive biological preparation of the present embodiment is interposed between cedar pollen and Ig E (immunoglobulin E), whereby their bonding is inhibited from taking place. As a result, the start of an allergic reaction is prevented. Therefore, by distributing either a nucleic acid or nucleic acid-derived substance to an adequate living body surface area, it becomes possible to isolate the negatively charged living body surface from a disease-state inducing substance because the distributed nucleic acid (or its derivative) and an allergen (such as pollen) whose surface is charged positive attract each other. This is an effective means for disease development prevention and reduction. Especially, it is possible to enhance the effect of contact prevention by forming a nucleic acid complex exhibiting a structure having a high affinity to an allergen and administrating it onto a living body mucous membrane, and by applying nucleic acids to a wearable means such as a mask, a goggle and so on covering an opening portion (mouth, eye, nose et cetera).

The contact preventive biological preparation of the present embodiment effectively exerts the above-described functions when used together with various types of electrolytes, the reason for which is that the separation/accumulation of nucleic acids and positively-charged disease-state inducing substances is promoted by the chaotropic effect of the electrolytes.

In addition, the micell formation of hydrophobic molecules by a surface active agent is effective for an affinity between the nucleic acid and the disease-state inducing substance.

Furthermore, DNA finds it difficult to develop but is a stable molecule, while on the other hand RNA is split in places, thereby being able to have various positional relationships with respect to foreign substances. Accordingly, it becomes possible for a nucleic acid biological preparation making use of these molecular characteristics to reinforce the function of enclosing foreign substances.

In addition, if a nucleic acid sequence having a high affinity to a disease-state inducing substance is selectively designed by screening, much better performance can be expected.

Besides, generally speaking, various types of medical agent components commonly used in the manufacture of biological preparations for external application may be used as an additive, in addition to the aforesaid nucleic acid components.

In the contact preventive biological preparation, at the time when developing a substance (e.g., a nucleic acid or derivative thereof) in a solvent, the substance is unevenly distributed in some cases by a disease-state inducing substance and by an ambient environment. As a result, the biological preparation becomes insufficient in penetration, emulsification, cleaning power, and refining power. In such a case, addition of any one of any other saccharide, a macromolecular compound, and a nonionic surface-active agent is effective.

As the macromolecular compound, for example, polyvinyl alcohol, polyvinyl pyrrolidone, hydroxyethyl cellulose, hydroxypropyl methylcellulose, methylcellulose, and cyclodextrin et cetera may be used. On the other hand, as the nonionic surface-active agent, polyoxyethylene higher fatty acid ester, polyoxyethylene sorbitan higher fatty acid ester, glycerin fatty acid ester, sorbitan fatty acid ester, cane sugar fatty acid ester et cetera may be used. More specifically, for example, polyoxyethylene hardened ricinus, polyoxyethylene sorbitan monooleate et cetera may be used.

These compounds may be used alone or in the form of a combination of two or more of them as required. In addition, the use of a chelating agent is effective to prevent water insolubilization by Ca or Mg. Lipase is effective for the decomposition of oil and fat components.

In addition, when forming a molecular structure which easily expands between nucleic acids by coexistence with a different saccharide (e.g., trehalose) capable of enhancing the property of development to a water solution, it is possible to safely improve the property of dispersion of the nucleic acid.

Because of this, it becomes possible to enhance the contact prevention effect of nucleic acids present in a solvent of the contact preventive biological preparation.

By the adding of the aforesaid saccharide, macromolecular compound, and nonionic surface-active agent, the biological preparation is improved in penetration, emulsification, cleaning power, and refining power to satisfactory levels. As the result of this, the contact preventive biological preparation is given improved latitude in the way of application as well as in the form of dosage.

When put in place around part of a living body, each of the aforesaid contact preventive biological preparations according to the present embodiment functions to effectively prevent contact of a disease-state inducing substance with the living body.

Here, the above-described contact preventive biological preparation application around the living body includes administration onto a surface area of the living body.

More specifically, the contact preventive biological preparations of the present embodiment are put in place around part of the living body in the following useful manners. That is, the contact preventive biological preparation is fixed to an attach means (e.g., mask, goggle, cap, clothes, air conditioner filter, tape) by an adequate technique, thereby being wearable by a sufferer.

On the other hand, in the case where the contact preventive biological preparation is administered onto a living body surface, it is effective that the biological preparation is distributed around a local area of the living body to which allergens and pathogens are liable to adhere. In other words, direct administration of the contact preventive biological preparation to a mucous membrane which is wet, which is not covered with any clothes, and in which Ig E antibodies or sugar chains appear on a living body surface or to a skin area, is an effective way. In view of this, as an applicable form of dosage, biological preparations for external application, such as an eyedrop biological preparation, nosedrop biological preparation, eardrop biological preparation, inhalant biological preparation, gargling biological preparation, spray biological preparation, liniment biological preparation, medical application biological preparation, cleaning biological preparation, intestinal infusion biological preparation et cetera, are preferable.

Embodiment 3

A contact preventive biological preparation for preventing contact of a disease-state inducing substance with a living body according to a third embodiment of the present invention contains a pectin. Alternatively, the contact preventive biological preparation of the present embodiment contains either a pectin-analogous uronic acid-containing polysaccharide which is a uronic acid-containing polysaccharide or pectin-derived substance which is a uronic acid-containing polysaccharide-derived substance and, in addition, either a nucleic acid or derivative thereof.

The pectin, pectin-analogous uronic acid-containing polysaccharide, nucleic acid, and nucleic acid-derived substance in the present embodiment are all negatively-charged, nature-origin water soluble macromolecules. For example, the aforesaid polysaccharides and nucleic acids have a commonality that they are not separated easily even after being subjected to an extraction process by phenol and chloroform and to an operational process of deposition by ethanol and acetic acid. And, pectins and nucleic acids are structures having palpable differences in molecular constituting element and three dimensional form.

Here, pectin has an esterification end and an oxidation end and possesses both hydrophobic and hydrophilic properties, while on the other hand nucleic acid is a hydrophilic molecule. Therefore, the aforesaid nucleic acid is separated and accumulated on its associated substance by the chaotropic effect, and exhibits a property of being selectively fractionated with respect to normal saccharides and proteins.

Pectins are substances in which any one of arabinose, xylose, fucose, rhamnose, and galactose or more than one of them (serving as a side chain) are bonded, in a comb fashion, to a rhamnose residue of rhamnogalacturonan (serving as a main chain). In other words, water molecules are taken into pectin as a group by hydrophobic hydration at the time of hydration based on the structural characteristics, as a result of which the concentration of nucleic acid in a free space is increased and, at the same time, positively charged ions, such as sodium salt, potassium salt, magnesium salt et cetera, are drawn to an uronic acid end.

Accordingly, the chaotropic effect is enhanced, therefore promoting the distribution of attraction bonding to nucleic acids present on a pollen surface. Furthermore, this phenomenon brings about a positive feedback effect which makes Cry j1 and Cry j2 conspicuous from a lipid structure in the pollen surface, thereby enhancing the enclosing of allergens by uronic acid-containing polysaccharide such as pectin to a further extent.

Here, typical uronic acids are glucuronic acid, galacturonic acid, mannuronic acid, iduronic acid, guluronic acid each of which has a structure having a carboxylic group formed by oxidation of part (which is a sixth alcohol group) of the chemical constitution of a monosaccharide (e.g., such as glucose, galactose, mannose, idose, gulose). As the uronic acid-containing polysaccharide, in addition to pectins abundantly occurring in vegetables and fruits, alginic acid abundantly occurring in seaweeds, and dermatan sulfate, chondroitin sulfate, chondroitin, hyaluronic acid, heparin et cetera abundantly occurring in animal's skin, cartilage, internal organ, are known, and they take charge of tissue protection and securement of moisturizing property and flexibility. In addition, these uronic acid-containing polysaccharides have compatibility so that they are recognized by a common enzyme because of the structural resemblance. Furthermore, these uronic acid-containing polysaccharides are found in daily-taken foods, therefore having no damaging effects on the human body functions. Likewise, pectins are also incorporated into every animal being as a plan, and there is no danger when externally applied to a living body or dosed.

When there exist a living body surface and an exogenous disease-state inducing substance in a reaction space, the disease-state inducing substance is contact-bonded to a recipient molecule on the living body surface and generates pathogenic stimulation. Here, in the case where either a uronic acid or nucleic acid intervenes independently in the reaction space, it surrounds the disease-state inducing substance (allergen) and masks it from the recipient molecule on the living body side, thereby making it possible to prevent occurrence of a contact reaction by attenuation. It is, however, inevitable that some disease-state inducing substances establish contact with a living body surface under non-uniformity in the modification factor on the periphery of a recipient molecule and in the disease-state inducing substance surface.

Here, in the case where uronic acid-containing polysaccharide and nucleic acid co-exist in a reaction space, the nucleic acid exerts such a characteristic property that it easily captures a positively-charged third-party substance and exerts a function of capturing foreign substances present around a disease-state inducing substance. Because of this, the disease-state inducing substance after removal of a mask of foreign substances therefrom is recognized definitely and surrounded by the uronic acid-containing polysaccharide. Accordingly, most of the disease-state inducing substances present in the reaction space are blocked off from the living body surface receptors, thereby making it possible to perfectly prevent contact reactions after that time. On the contrary to this, hydrophobic foreign substances are liable to be recognized by uronic acid-containing polysaccharide.

Also with respect to pathogens such as viruses, the envelop and protein spikes are well coated by the same mechanism. In other words, approach molecules present on the virus surface to living cells are placed in an environment in which they are not allowed to establish contact with a living body. Besides, when facing a group of molecules present on a living body surface and having different protein structures and charge characteristics, a nucleic acid having a single negative charge per nucleotide and a pectin that exhibits an ester or oxidation end in a regular or random order in a polysaccharide sequence exert an excellent function of selecting, from among groups of molecules of high isoelectric point, groups having different characteristics.

Taking these into consideration, the coexistence of any one of a pectin, pectin-analogous uronic acid-containing polysaccharide, and pectin-derived substance with either one of a nucleic acid or nucleic acid-derived substance as a main functional component results in a biological preparation which is biologically excellent and practical in executing a molecule selection based on the affinity to uronic acid-containing polysaccharides or the affinity to nucleic acids as well as in preventing contact of a disease-state inducing substance with a living body.

In addition, the aforesaid contact preventive biological preparations prove effective for inflammatory skin disorders such as atopic dermatitis. In inflammatory skin disorders such as atopic dermatitis, various types of cytokines are emitted from inflammatory cells and such cytokines either irritate skin surface cells et cetera or cause damage thereto. Because of this, the inflammatory cells again wonder and a vicious cycle is activated to accelerate the increase in deterioration of symptoms such as itching and inflammation, which is a disease forming factor.

Here, if the biological preparation of the present embodiment which contains either a pectin or pectin-analogous uronic acid-containing polysaccharide and a nucleic acid is applied or administrated by spraying to an inflammatory site, this exerts such an action that the pectin (pectin-analogous uronic acid-containing polysaccharide) and nucleic acid adsorb and cover inflammatory secretions emitted and distributed in a skin surface area and cover various irritating substances coming into contact with the skin inflammatory area from the outside for protecting the skin surface.

Especially, in an inflammatory cell which has once developed atopic symptoms, the barrier function of its cell membrane is insufficient. To cope with this, inflammatory components are adsorbed from outside the cell by the contact preventive biological preparation according to the present embodiment, thereby achieving the stabilization of cell membranes and further the stabilization of cell functions. In addition, the nucleic acid is useful for vicious circle prevention because it has a general affinity to a signal molecule which is transmitted into the cell nucleus.

The feature of the coexistence of pectin with nucleic acid is based on the multiplication of a function of capturing inflammatory secretions and exogenous irritants by the chaotropic effect owing to the increase in hydration and ionic strength by cooperation of the pectin and nucleic acid. Employing a uronic acid alone provides a sticky use feeling when applied to the living body. On the other hand, employing a nucleic acid alone clearly results in the reduction in effect. Accordingly, the pectin/nucleic acid coexistence is significant.

The contact preventive biological preparation of the present embodiment, which contains any one of a pectin, pectin-analogous uronic acid-containing polysaccharide, and their derivative and either a nucleic acid or nucleic acid-derived substance, brings out an excellent effect when put in place, as a biological preparation for external application, around part of the living body.

Here, the above-described contact preventive biological preparation application around the living body includes administration onto a living body surface area. More specifically, the above-described contact preventive biological preparation contains any one of a pectin, pectin-analogous uronic acid-containing polysaccharide, and their derivative and, in addition thereto, either a nucleic acid or nucleic acid-derived substance, is used as a biological preparation for external application in any one of dosage forms including an eyedrop biological preparation, nosedrop biological preparation, eardrop biological preparation, inhalant biological preparation, gargling biological preparation, spray biological preparation, liniment biological preparation, medical application biological preparation, cleaning biological preparation, intestinal infusion biological preparation. In addition, the contact preventive biological preparation is applicable to any one of wearable means including a mask, goggle, cap, clothes, air conditioner filter, tape and they are effective for preventing the manifestation of diseases.

Furthermore, various types of biological preparations for external application comprising both of a pectin and a nucleic acid each exhibit a unique bonding affinity and exert a function of getting out an affinity mutually for the both. To sum up, since a nucleic acid or nucleic acid-derived substance exerts an action of adsorbing and eliminating a variety of foreign substances present on the surface of a disease-condition causing substance, this maintains a space environment allowing a uronic acid-containing polysaccharide to easily recognize an allergen and other pathogen-origin enzyme proteins.

On the other hand, since uronic acid-containing polysaccharides exert a function of adsorbing and eliminating a variety of foreign substances present on the surface of various types of cancer-causing substances, this permits a nucleic acid or nucleic acid-derived substance to recognize such disease-state inducing substances such as a cancer-causing substance, with ease. In other words, if pectin and nucleic acid are present mixedly, this is useful for forming a biological preparation capable of improvement in determining various disease-state inducing substances and of disease manifestation avoidance.

In the contact preventive biological preparation according to the present embodiment, at the time when developing a substance such as pectin, pectin-analogous uronic acid-containing polysaccharide and their derivative and another substance such as nucleic acid and nucleic acid-derived substance, in a solvent, these substances are unevenly distributed in some cases by a disease-state inducing substance and by an ambient environment. As a result, the biological preparation becomes insufficient in penetration, emulsification, cleaning power, and refining power. In such a case, addition of any one of another saccharide, a nonionic surface-active agent, and a macromolecular compound to the biological preparation is effective.

As the macromolecular compound, for example, polyvinyl alcohol, polyvinyl pyrrolidone, hydroxyethyl cellulose, hydroxypropyl methylcellulose, methylcellulose, and cyclodextrin et cetera may be used. On the other hand, as the nonionic surface-active agent, polyoxyethylene higher fatty acid ester, polyoxyethylene sorbitan higher fatty acid ester, glycerin fatty acid ester, sorbitan fatty acid ester, cane sugar fatty acid ester et cetera may be used. More specifically, for example polyoxyethylene hardened ricinus, polyoxyethylene sorbitan monooleate et cetera may be used.

These compounds may be used alone or in the form of a combination of two or more of them as required. In addition, the use of a chelating agent is effective to prevent water insolubilization by Ca or Mg. Lipase is effective for the decomposition of oil and fat components.

In addition, when forming a molecular structure which easily expands between pectins or between nucleic acids by coexistence with a different saccharide (e.g., trehalose) capable of enhancing the property of development to a water solution, it is possible to safely improve the property of dispersion of the pectin or nucleic acid. Because of this, it becomes possible to enhance the contact prevention effect of a pectin, nucleic acid, or their derivative present in a solvent of the contact preventive biological preparation.

By the adding of the aforesaid macromolecular compound and nonionic surface-active agent, the biological preparation is improved in penetration, emulsification, cleaning power, and refining power to satisfactory levels. As the result of this, the contact preventive biological preparation of the present embodiment is given improved latitude in the way of application as well as in the form of dosage.

Embodiment 4

A contact preventive biological preparation according to a fourth embodiment of the present invention comprises a contact preventive biological preparation according to each of the foregoing embodiments which contains therein an antiallergic agent such as an antihistamic agent.

The contact preventive biological preparation of the present embodiment complements the function of preventing contact of a disease-state inducing substance with a living body surface of the contact preventive biological preparations of the foregoing embodiments and either prevents the development of allergic symptoms or subsides them. As the antiallergic agent such as an antihistamic agent, conventionally used curative medicines can be used.

At the point of time when the contact preventive biological preparation is used, there are cases where the living body has already been exposed to large amounts of disease-state inducing substances. In addition, it is possible to consider such a case that a new disease-state inducing substance arrives at the stage in which a contact preventive biological preparation used is withdrawing from a local part to which the contact preventive biological preparation had been applied. In these cases, for the contact preventive biological preparations of the foregoing embodiments, there is the possibility that the capturing of disease-state inducing substances becomes insufficient.

In such a case, in accordance with the contact preventive biological preparation of the present embodiment, the antiallergic agent added thereto either inhibits the development of a symptom caused by an escaped disease-state inducing substance or relieves the symptom. Accordingly, the components of the antiallergic agent exert a function of complementing the disease development inhibiting function of the foregoing contact preventive biological preparation which inhibits the manifestation of diseases. In addition, in cases where there is the possibility that an edema or exudate appearing on a living body surface prevents the development of the contact preventive biological preparation, it is possible to contain a medicinal component capable of removal of the edema.

As described above, the combination of various types of medical components having respective action points with respect to various cell reactions with the contact preventive biological preparations of the present invention is not incompatible with the functions of preventing contact of a disease-state inducing substance with a living body of the contact preventive biological preparations but serves as an important biological preparation constituting means for complementing these functions.

The contact preventive biological preparation formed in accordance with the present embodiment is applicable to various biological preparations for external application such as eyedrops, nosedrops, eardrops, inhalant agents, spray agents, intestinal infusion agents, and bath agents. In addition, in a method of preventing contact of a disease-state inducing substance with a living body by various means including biological preparations (eyedrops, nosedrops, eardrops, inhalant agents, mouthwash agents, bath agents, and intestinal infusion agents), antiallergic agents such as an antihistamic agent prevent or reduce the development of allergic symptoms.

Exemplary Embodiments

Hereinbelow, exemplary embodiments of the present invention will be described in detail. It should be noted that the prevent invention will not limited at all to the following exemplary embodiments.

Exemplary Embodiment 1

Assay of Pollen Enclosure by Pectin and Nucleic Acid (Confirmation of Pollen Rouleaux Formation)

In order to assay the actions of pectin and nucleic acid, contained in the contact preventive biological preparation of the present invention, on pollen, the following experiments were carried out. In the following experiments, by "pollen rouleaux formation" is meant a state in which a plurality of pollen particles continue linearly, and by "pollen aggregation" is meant a state in which a plurality of pollen particles constitute a bulk. Both "pollen rouleaux formation" and "pollen aggregation" denote a state in which pollen particles are captured by a medium and their free movement is inhibited, and as the degree thereof increases, the power of enclosing pollen increases.

Japan cedar pollen was put in a first water solution containing pectin (#168-00555 by Wako Pure Chemical Industries, Ltd.), in a second water solution containing glycerin, in a third water solution containing pectin and glycerin, and in a fourth water solution containing DNA (DN-JA0904, DK-JB0218 by Daiwa Fine Chemical Co. Ltd.), RNA (R6625 by Sigma), amino acid, and glycerin, and these water solutions were subjected to incubation for ten minutes at room temperature to prepare pollen developed liquids.

Each pollen developed liquid was instilled in the form of a drop onto a slide glass and was allowed to stand. After being dried, the test sample was stained by means of a ruthenium red solution and a gentian violet alcohol solution, and the assay of pollen rouleaux formation was examined microscopically.

In such a state that no pectin was present or present at a low concentration of less than 0.3%, no rouleaux capture of cedar pollen was detected. When there was made an increase in the concentration of pectin up to from about 0.03 to about 3.0%, pollen rouleaux formation was promoted.

In addition, the effects of DNA and RNA which are nucleic acids on the enclosure of pollen was examined. DNA and RNA individually exhibited an action of causing pollen to aggregate partially at concentrations of 0.5% or above.

Furthermore, when either DNA or RNA was added, in the proper proportions, to the aforesaid low-concentration (below 0.03%) pectin water solution unable to provide a satisfactory pollen enclosure, a rouleaux formation was detected, and the enclosure of pollen by pectin was promoted significantly. Furthermore, by the adding of DNA of a low concentration (about 0.1 to 0.3%) to a 0.2% pectin containing water solution, a strong aggregation of pollen was observed.

Besides, the action of pectin was reinforced by carboxymethyl cellulose, methyl cellulose, trehalose, and cluster dextrin. In addition, sugar ester and polygly ester exert an effect of causing aggregated or nummular pollen to disperse. Various types of amino acids have properties of causing pollen to tend to burst, while on the other hand glutamic acid and asparaginic acid function to reinforce the action of enclosing pollen by pectin. Furthermore, although boric acid promoted the aggregation of pollen but exerted an action of causing pollen to burst.

Exemplary Embodiment 2

Comparative Examinations of Pollen Enclosing Actions by Various Pectins, Uronic Acid Containing Substances, and Mucopolysaccharides In order to comparatively examine the actions of enclosing pollen by pectins, uronic acid-containing substances, and mucopolysaccharides according to the present invention, the following twelve kinds of samples were examined in the same way as the first exemplary embodiment. The twelve samples were: YM115-H; LM101-AS; Type DF; SLENDID type 100; SLENDID type 200; LM104AS-FS; LM-5CS; USP-H; USP-L; LH-105AS; AS Confectionary; and YM150-LJ by Genu.

For these twelve different samples, approximately all of the pectin matters were found to have the power of enclosing pollen; however, carrageenan (K-100J) was found to be less significant in pollen enclosing power than the others. The degree of esterification in these pectins ranged widely from 15% up to 74%. The examination results gave suggestions that pectins have a capability of enclosing pollen as their universal property, and that such a pollen enclosing capability is relatively specific to pectins among the analogous uronic acid containing substances.

Here, extracts from various kinds of plants were obtained for examining the action of each extract and the interaction of each extract with pure pectin. For extracts from kudzu, mekabu (seaweed root), aloe, and mozuku (*Nemacystus decipiens*), partial pollen aggregations were observed when used alone or together with a pectin. However, none of them exerted a rouleaux formation action comparable to the pollen rouleaux formation exerted by pure pectin.

On the other hand, the pollen enclosing interaction of an electrolyte, antihistamic agent, sterilizing substance, biological preparation, or commercially available admixture and pectin was examined. The examination results showed that the pollen enclosing function of the pectin was exerted satisfactorily without any interference in biological preparations containing various components (artificial tears, nose spray, mouth washer et cetera) and in various drug solutions containing a mixture thereof.

Exemplary Embodiment 3

Examination of the Actions of Pectin and Nucleic Acid on In Vitro Cluster Formation by Pollenosis Sufferer's White Blood Cells and Pollen In order to examine the actions of pectin and nucleic acid according to the present invention on the pollenosis sufferer's white blood cells and pollen, the following experiments were carried out.

White blood cells separated from the blood of a pollenosis sufferer was subjected to incubation on a slide glass with cedar pollen fixed thereonto. An accumulation of a great number of while blood cells and emission of granules were found in pollen dispersed in pure water, while on the other hand white blood cells had no tendency to accumulate on pollen dispersed in a 0.3% pectin water solution and thereafter fixed to a slide glass.

To sum up, pectin prevents white blood cells of a pollenosis sufferer from bonding to pollen, as a result of which the emission of granules from the white blood cells and the accumulation of many different kinds of white blood cells are prevented. This in vitro experiment result shows that, in a vital reaction site, pectin prevents the sudden occurrence of allergic reactions caused by cedar pollen wherein the inhibition of pollen recognition by white blood cells containing basophiles is a point of action.

On the other hand, also for the case of a 0.5% DNA solution (Daiwa Fine Chemical Co. Ltd.), there was observed a tendency that the accumulation of white blood cells to pollen was inhibited partially. The most conspicuous one was a solution comprising 0.5% pectin and 0.5% DNA. In this solution, the surface of a pollen grain was entirely covered in strip fashion with DNA and pectin, and no white blood cells were allowed to reach the pollen grain. Unlike ordinary micro molecules, a single nucleotide of the nucleic acid has a single negative charge and the entirety of the macromolecule is charged heavily negative. Accordingly, it is determined such that the nucleic acid entirely covers, in a strip fashion, positively charged pollen, together with pectin, thereby exerting a function of preventing an allergen from adhering to the surface of negatively charged white blood cells.

Exemplary Embodiment 4

Examination of the Actions of Pectin and Nucleic Acid on the Emission of Histamine from Basophiles in the Blood of a Pollenosis Sufferer In order to examine the actions of the pectin and nucleic acid of the present invention on the emission of histamine from basophiles in the blood of a pollenosis sufferer, the following experiments were carried out.

Blood sampling from a pollenosis sufferer was carried out, and basophiles recognized by a cell surface marker were separated by means of a magnet method. Then, the basophiles thus separated were exposed to a pollen extraction component fixed onto a micro plate, and emitted histamine was quantitatively measured by an absorbance method through a coloring reaction making use of antihistamic antibodies (HRT by Shionogi & Co., Ltd.).

A control sample making use of only a buffering solution, a sample comprising a pectin-containing buffering solution, and a nucleic acid-containing sample were prepared, and the rate of liberation of histamine with respect to the increase of allergen was comparatively examined. In the experiment, a cedar pollen extraction antigen was used as an allergen.

FIG. 1 graphically represents a relationship between the concentration of cedar pollen extraction antigen (allergen) and the rate of liberation of histamine. In the graph of FIG. 1, white circles show results about the 0.03% pectin containing sample whilst black circles show results about the control sample using only a buffering solution.

As shown in FIG. 1, in the pectin-containing sample the liberation of histamine from basophiles at the time of immediate stimulation by a cedar pollen extraction antigen was inhibited over a wide range. It is understandable that in the 0.03%-concentration pectin solution the liberation of histamine from basophiles with respect to a cedar pollen extraction antigen of moderate concentration is inhibited effectively.

Likewise, a high-concentration pectin containing sample (from about 0.1% to about 0.3%) was examined, and the examination results showed that the liberation of histamine by high-concentration cedar pollen was also inhibited. In addition, by the same experiment both of DNA and RNA proved to be able to inhibit the liberation of histamine by basophiles from a pollenosis sufferer at the time of pollen allergen stimulation.

FIG. 2 is a diagram graphically representing a multiplicative relationship of pectin and DNA with respect to the effect of inhibiting the rate of liberation of histamine. As can be seen from FIG. 2, it is impossible for a 0.03% pectin-containing sample alone to provide a satisfactory effect of preventing the liberation of histamine. However, by adding DNA so that the concentration becomes 0.3%, a significant histamine liberation preventing effect was obtained.

In addition, also by adding RNA instead of DNA, the liberation of histamine caused by a pollen extract was inhibited significantly.

Exemplary Embodiment 5

Examination of the Actions of Pectin and Nucleic Acid on the Enzymatic Activity of Influenza-Virus Neuraminidase In order to examine the actions of the pectin and nucleic acid of the present invention affecting the enzymatic activity of neuraminidase of the influenza virus, the following experiment was carried out.

The activity of neuraminidase of the type A influenza virus was analyzed by an enzymic reaction with a synthetic coloring substrate (Gene Stat Flu Kit by Nichirei). This enzymic reaction is based on the power of neuraminidase to cut acetyl neuraminic, and darker solution's blue-coloring result indicates higher enzymatic activity.

A virus test body, taken from the larynx of a type A influenza infected patient, was divided into two sample pieces, i.e., a control sample and a sample used for the evaluation of the anti-enzyme activity of pectins. For the case of a control sample in a reaction solution with an addition of 300 μl distilled water, vivid blue-coloring was exhibited by instillation of a test solution. On the other hand, for the case of an evaluation sample with an addition of 0.05% pectin (USD-H by Genu) to a neuraminidase-active, positive test body, no color reaction was observed in the same reaction solution at all (negative).

To sum up, the experiment proved that, even at a low concentration such as 0.05%, pectins succeeded to deactivate the neuraminidase enzymic activity of influenza with respect to the neuraminidase substrate. This showed that pectins brought out an action of preventing the emission of virus particles from infected cells during the multiplication rotation of influenza viruses.

In addition, the same experiment was carried on a heparin-containing evaluation sample of 20 unit/ml. The experiment results for the case of the heparin-containing evaluation sample showed that the color exhibition of blue coloring became dull.

Furthermore, the experiment results for the case of a 0.5% DNA-containing evaluation sample showed that the neuraminidase enzymic activity was enhanced in comparison with the control sample.

It is understandable from the above that uronic acid-containing polysaccharides (e.g., pectin and heparin) attenuate the neuraminidase enzymic activity of influenza viruses while on the other hand nucleic acids have an action of accelerating the identification of uronic acid-containing substrates (pectin and heparin) by neuraminidase. Accordingly, when nucleic acids are involved, the pectin recognition capability of neuraminidase is improved.

Exemplary Embodiment 6

Application Testing of Eyedrop and Nosedrop Biological Preparations on Pollenosis Sufferer The contact preventive biological preparation according to the present invention was applied to eyedrop and nosedrop biological preparations and their application tests were carried out on test subjects. These eyedrop and nosedrop biological preparations according to the present exemplary embodiment contain therein pectin (type DF et cetera by Genu) and DNA (Daiwa Fine Chemical Co. Ltd.) at the following contents.

The content of pectin and the content of DNA are: pectin (0.03 to 1.0%); DNA (0.05 to 1.0%); 0.5% pectin+0.5% DNA; 0.8% pectin+0.2% DNA; and 0.2% pectin+0.8% DNA.

Pollenosis sufferers were test subjects, and the degree of improvement in itching symptom when each eyedrop biological preparation was administrated at the time of the development of an allergic reaction and its duration and application (use) feeling (the degree of uncomfortable feeling) were examined. The results thus obtained were evaluated according to the following evaluation standards.

Evaluation Standards for the Degree of Improvement in Itching

AAA: itching was subsided to a remarkable degree
AA: itching was subsided
A: itching was subsided to some degree
BB: itching as before
B: itching worsened Evaluation Standards for the Degree of Duration of Improvement in Itching AAA: lasted for 180 minutes or longer
AA: lasted for 120 minutes or longer
A: lasted for 60 minutes or longer
BB: lasted for 30-60 minutes
B: lasted for less than 30 minutes Evaluation Standards for Application Feeling (the Degree of Uncomfortable Feeling)

AAA: no uncomfortable feeling at all
AA: almost no uncomfortable feeling
A: “difficult to tell”
BB: bothered by a uncomfortable feeling
B: bothered very much by a uncomfortable feeling Evaluation Standards for the Degree of Improvement in Symptom at the Time of Going-Out AAA: itching was subsided to a remarkable degree
AA: itching was subsided
A: itching was subsided to some degree
BB: itching as before
B: itching worsened Effect when Applied at Bedtime and the Degree of Improvement in Symptom in the Following Morning AAA: itching was subsided to a remarkable degree
AA: itching was subsided
A: itching was subsided to some degree
BB: itching as before
B: itching worsened Effect when Applied at Bedtime and the Degree of Improvement in Snuffles in the Following Morning AAA: snuffles was subsided to a remarkable degree
AA: snuffles was subsided
A: snuffles was subsided to some degree
BB: snuffles as before
B: snuffles worsened As can be seen from the above, it was confirmed that pectin (from 0.03 to 1%) and DNA (from 0.05 to 1%) each have, when used alone, curative properties against pollenosis symptoms typified by itching and snuffles.

Referring now to FIG. 3, there are shown results of application tests of eyedrop biological preparations containing 0.5% pectin, 0.5% DNA, 0.5% pectin+0.5% DNA, 0.8% pectin+0.2% DNA, and 0.2% pectin+0.8% DNA, respectively.

As shown in FIG. 3, both pectin and DNA exert obvious curative properties against the symptoms. Besides, when a mixture of pectin and DNA was administered, curative properties against the pollenosis symptoms were confirmed even when the concentration was at lower levels. However, eyedrops of a pectin concentration of 0.5% or more caused a sticky feeling. On the other hand, when DNA was used alone, the effect of improving symptoms is somewhat insufficiency.

Exemplary Embodiment 7

Comparison in Action with Commercially Available Eyedrop and Nosedrop Biological Preparations Conventional, commercially available eyedrop and nosedrop biological preparations against pollenosis symptoms were compared with the biological preparations according to the present invention in the action with respect to the manifestation of pollenosis symptoms.

The commercially available nosedrop biological preparations contain a vasopressor agent, an antihistamic agent, a bactericidal substance, a fragrant material et cetera.

In the application of such a commercially available nosedrop biological preparation, it gave quick relief while on the other hand giving burning sensation, dying sensation, and pain. In addition, the symptoms recurred in a short period of time after the application, for example after an elapse of about one hour.

Furthermore, for the case of the commercially available nosedrop biological preparation, when used at bed time some test subjects had a uncomfortable feeling in their nasal cavities and were awakened in the night due to the snuffles or the like.

In addition, the commercially available eyedrop biological preparations had no effect on the snuffles. The commercially available eyedrop biological preparations temporarily subsided itching paraesthesia; however, the symptoms recurred soon when the subject was exposed to new pollen antigens in outdoor environments.

On the contrary, eyedrops and nosedrops containing the biological preparations according to the present invention were free from irritation in any combination and there was an interval of from 10 to 15 minutes until the manifestation of their effects. The duration of effect of the eyedrops and nosedrops containing the biological preparations according to the present invention exceeded three hours and allergy symptoms, such as itching, snuffles, and runny nose, were eliminated when administrated four to five times a day.

Furthermore, in the case where eyedrops and nosedrops containing the biological preparations according to the present invention were applied at bedtime, test subjects had a pleasant sleep and were relieved from the snuffles and itching in the following morning. Of these biological preparations, one that contains both DNA and pectin proved to be superior in the degree of subsiding the snuffles and itching symptoms and in the level of comfort in the following morning.

At the time when pectin was used alone, the test subject had a felling of drying supposedly resulting from the absorbing of moisture from peripheral areas in a relatively early stage. On the other hand, at the time when DNA was used alone, there was the tendency that the maintaining of a symptom preventive effect became incomplete. In the case where a pectin containing biological preparation and a DNA containing biological preparation were used alternately at intervals of 5 to 15 minutes, pollenosis symptoms such as itching paraesthesia in eyes and the snuffles were almost completely prevented during the "going-out" in the daytime. When a mixed biological preparation of pectin and DNA was used, the manifestation of symptoms was prevented by using the mixture several times in the daytime in a room, and when going out, the mixture proved to be sufficient if used additionally two or three times.

The effect of subsiding the symptoms was reinforced by adding, in the proper portions, chlorpheniramine maleate, glycyrrhizin, pyridoxine, naphazoline hydrochloride, and benzalkonium chloride, to the eyedrop and nosedrop biological preparations of the foregoing exemplary embodiment.

Exemplary Embodiment 8

Mask and Spray Used for Mask for the Capturing of Disease-State Inducing Substances The contact preventive biological preparation of the present invention was applied to a mask, and testing to assay the effect of capturing disease-state inducing substances was carried out.

A water solution containing 0.5% pectin and 0.5% DNA was prepared. One to three sheet-like pieces of cotton gauze were placed in the water solution prepared. These cotton gauze pieces were put between dried cotton gauze pieces and mounted to a commercially available mask to form a mask for the capturing of disease-state inducing substances.

In addition, a water solution containing 0.5% pectin and 0.5% DNA was filled in a spray container to form a spray for masks. A commercially available mask was sprayed with the water solution from the mask spray in a proper amount to form a mask for the capturing of disease-state inducing substances.

The above-described two types of masks were worn by test subjects. The test subjects were taken out to an outdoor environment where the amount of scattering of pollen was great. The results showed that any allergic symptoms were not detected at all in the nasal cavity as well as in the buccal cavity when wearing any one of the two types of masks.

The results proved that the biological preparation containing pectin and DNA according to the present exemplary embodiment was applicable to filters for effectively capturing disease-state inducing substances. Accordingly, if a filter making utilization of the biological preparation of the present exemplary embodiment is used in an indoor and outdoor air supplying/ventilating system or in an exhausting system, this makes it possible to prevent the incoming of disease-state inducing substances into an indoor space, to prevent disease-state inducing substances from scattering in the room, and to provide an effect in removing disease-state inducing substances present in the room.

Exemplary Embodiment 9

Gargling Biological Preparation for the Capturing/Cleaning of Disease-State Inducing Substances The contact preventive biological preparation according to the present invention was applied to a gargling biological preparation and testing to assay the effect of cleaning the buccal cavity and larynx was carried out.

A water solution containing therein 0.05% pectin and 0.05% DNA was prepared to form a gargling biological preparation. Testing, in which the test subject cleaned his/her buccal cavity and larynx with the water solution by gargling, was carried out. The test subject was not bothered by any uncomfortable after-use feeling and excellent rinsing was executed. In addition, even when the water solution was mixed with a disinfectant such as Popidon Yodo of normal application concentration or with a solution of azulene, the test subject was not bothered by any uncomfortable feeling.

Exemplary Embodiment 10

Synergistic Effect Found in a Compound Product of Antiallergic Agent and Contact Preventive Biological Preparation for Preventing Contact of Disease-State Inducing Substance with Living Body Testing to assay the synergistic effect of the contact preventive biological preparation of the present invention and an antiallergic agent was carried out.

Sodium cromoglycate (1.0%) as an antiallergic agent was added to a water solution containing 0.5% pectin and 0.5% DNA to form an eyedrop biological preparation. This eyedrop biological preparation was administered to the eyes of a test subject who had developed a pollen allergy. The effect of improving the symptoms appeared quickly and there was no problem with the feeling of use. By comparison with the case where sodium cromoglycate was used alone, more significant effects were observed both for the degree of improvement in symptom and for the duration of effect in the eyedrop biological preparation according to the present invention.

Exemplary Embodiment 11

Synergistic Effect Found in a Compound Product of Steroid Agent and Contact Preventive Biological Preparation for Preventing Contact of Disease-State Inducing Substance with Living Body Testing to assay the synergistic effect of the contact preventive biological preparation of the present invention and a steroid agent was carried out.

Betamethasone phosphate (0.005%) as a steroid agent was added to a water solution containing 0.5% pectin and 0.5% DNA to form an eyedrop biological preparation. This eyedrop biological preparation was administered to the eyes of a test subject who had developed a pollen allergy. The effect of improving the symptoms appeared quickly and the feeling of use was excellent. By comparison with the case where betamethasone phosphate was used alone, more significant effects were observed both for the degree of improvement in symptom and for the duration of effect in the eyedrop biological preparation according to the present invention.

Exemplary Embodiment 12

When Used as Inhalant Liquid

Testing to assay the effect of the contact preventive biological preparation of the present invention when used in the form of an inhalant liquid was carried out.

A water solution containing 0.05% pectin and 0.05% DNA was prepared, and the water solution was used in a simulated manner, wherein the capturing of disease-state inducing substances by inhalation and the treatment of rinsing from the pharynx to the bronchia by means of a ultrasonic nebulizer were performed. None of the test subjects had an after-use uncomfortable feeling and an excellent inhalation treatment was executed. Even when mixed with a bronchodilator or with a water solution of an expectorant agent, any after-use uncomfortable feeling was not reported. Accordingly, this suggests that even in the case where disease-state inducing substances actually exist in the bronchi cavity they can be discharged outside in the form of coughed-up sputum.

Exemplary Embodiment 13

Curative Biological Preparation for Inflammatory Dermatitis Including Atopic One Testing to assay the effect of the contact preventive biological preparation of the present invention in the form of an inflammatory dermatitis curative biological preparation was carried out.

0.2% pectin (0.8% DNA-sodium salt, 0.8% pectin, 0.2% DNA-sodium salt) was instilled in the form of a drop to an inflammatory eczematous local part of the inside bend of the left elbow of a test subject who had developed chronic atopic dermatitis. Skin itching with pain before the administration was disappeared completely after an elapse of 2-3 hours. The effect continued from the following day on. The skin eczema of the test subject was improved to such a state that it was indistinctive in appearance from other normal local parts of the patient's body.

Embodiment 5

A biological preparation according to a fifth embodiment of the present invention is a curative agent for endogenous factors such as an internal secretion disturbing substance. More specifically, the biological preparation of the present embodiment is a curative biological preparation for use in the treatment of skin or mucous membrane inflammatory diseases which comprises at least either uronic acid-containing polysaccharide or nucleic acid. In other words, the curative biological preparation of the present embodiment contains any one of uronic acid-containing polysaccharide and nucleic acid or both of them.

Of the uronic acid-containing polysaccharides, especially one that has a structure with a side chain is able to enclose a foreign element within its stereo structure. Actually, it is believed that this characteristic is concerned with the uniform distribution of insoluble components in a liquid solution such as yoghurt and jam (jelly).

Furthermore, nucleic acids absorb even micro molecules into gaps of its double helix structure, in addition to attraction by charge.

On the other hand, it is believed that inflammatory cycles such as the emission of chemical mediators such as endogenous histamine and leutriene and the productive sthenia of cytokines including IL-3, IL-5, IL-6, IL-10, IL-13, and TNF-α, and the functioning of unknown intermediate molecules or great molecules have great influence on the mucous membrane inflammation.

The biological preparation which contains either uronic acid-containing polysaccharide or nucleic acid entraps various types of inflammation related substances, regardless of the type of these inflammation related substances, within its stereo structure and masks them from the mucous membrane or inflammatory cells, thereby bringing out an action capable of eliminating inflammation around the mucous membrane or leading it in remission.

The content of functional components in the biological preparation is as follows. For the case of pectin which is a uronic acid-containing polysaccharide, the pectin concentration in the biological preparation preferably ranges between 0.03% and 3%, most preferably between 0.1% and 1%. For the case of DNA which is a nucleic acid, the DNA concentration in the biological preparation preferably ranges between 0.03% and 3%, most preferably between 0.05% and 1%.

Especially, for the case of curative biological preparations for conjunctivitis containing either uronic acid-containing polysaccharide or nucleic acid, it is believed that various chemical mediators, cytokines, and unknown intermediate molecules or macro molecules perform functions on inflammatory symptoms such as acute or chronic bulbar conjunctiva congestion and edema and subsequent cell proliferation, regardless of the cause of disease.

Conventional medical treatments by means of instillation of drop using an anti-inflammatory micro molecule biological preparation have an effect on an inflammatory mechanism on the living body side, and it is difficult for these treatments to completely inhibit congestion, edema, and cell proliferation. Besides, if administrated in large amounts, this may cause a cell functional disorder.

On the contrary, the instillation of drop of a biological preparation containing either uronic acid-containing polysaccharide or nucleic acid makes it possible to entrap various types of inflammation related substances, regardless of the type of these inflammation related substances, within a stereo structure by a mechanism completely different from that of the conventional eyedrop biological preparations and to mask them from the mucous membrane or inflammatory cells, thereby eliminating inflammation around the conjunctiva or leading it in remission.

In addition, the biological preparation of the present embodiment, because of its ester structure having a side chain, is able to capture not only a water-soluble inflammation related substance but also a fat-soluble inflammation related substance, thereby exerting an effect different from that of the conventional biological preparations. From the viewpoint of the feeling of use and the efficacy of the biological preparation of the present embodiment, the content of functional components in the biological preparation is as follows. For the case of pectin which is one of the uronic acid-containing polysaccharides, the pectin concentration in the biological preparation preferably ranges between 0.03% and 3%, most preferably between 0.1% and 1%. For the case of DNA which is one of the nucleic acids, the DNA concentration in the biological preparation preferably ranges between 0.03% and 3%, most preferably between 0.05% and 1%.

In addition, in order to protect a living body from various poisonous substances such as cancer-causing substances and internal secretion disturbing substances the present biological preparation may be applied to products wearable to the human body such as filter and mask.

Although workplaces and ordinary living environments are full of internal secretion disturbing substances as typified by ethidium bromide, dioxin, PCB, asbestos (fire proof material), benzene (contained in gasoline), toluene, cyclohexane, vinyl chloride (material for polyvinyl chloride), cigarette, benzpyrene (exhaust gas), aflatoxin (such as peanut mold poison), tar, nitrosamine, formaldehyde (which is supposed to be a cause of the sick house syndrome occurring in a newly-built house), poisonous cancer-causing substance (diesel exhaust gas), various dioxins, tributyltin, 4-octylphenol, nonylphenol, di-n-butyl phthalate, octachlorostyrene, benzophenone, dicyclohexyl phthalate, di(2-ethylhexyl) phthalate, and four substances (butyl benzyl phthalate, diethyl phthalate, di(2-ethylhexyl) adipate, and triphenyltin), we are not able to recognize these substances and, as a result, are exposed to them without being aware.

Of the uronic acid-containing polysaccharides of the present biological preparation, especially one that has a structure having an ionic character and an ester type side chain is conceivably able to enclose various cancer-causing substances and internal secretion disturbing substances in its stereo structure.

In addition to the above, nucleic acids are able to absorb cancer-causing substances and internal secretion disturbing substances into gaps defined in its double helix structure and to bond strong ionic molecules. Therefore, biological preparations containing both of uronic acid-containing polysaccharide and nucleic acid are useful for protecting a living body from poisonous substances.

Exemplary Embodiment 1

An eyedrop biological preparation containing 0.5% pectin and 0.5% DNA was administered to a 67-years-old female patient with conjunctivitis with an uncomfortable feeling and binocular congestion who had a bilateral cataract operation three months before. The eyedrop biological preparation was instilled to the patient three times a day, which improved the degree of eye bloodshot condition and uncomfortable feeling, and from the following day the eye bloodshot condition disappeared completely. The administration of the eyedrop biological preparation was discontinued after an elapse of three weeks. Then the eyes of the patient became bloodshot again in three days. The administration of the eyedrop biological preparation was resumed and, as a result, the symptoms disappeared. This proves that the present biological preparation has a significant effect on the disease conditions of mucous membrane inflammation.

Exemplary Embodiment 2

A piece of nonwoven cloth was impregnated with a pectin (USPL 1%) water solution. Thereafter, the nonwoven cloth piece was dried. A filter (8 cm in diameter) was cut out from the piece. Here, another piece of nonwoven cloth treated with distilled water was used as a control for the sake of comparison. Toluene (concentration: 100 ppm) or cyclohexane (concentration: 100 ppm) was loaded to the pectin-impregnated nonwoven cloth piece at a flow rate of 15 L/min. The result showed that the concentration of toluene (cyclohexane) was decreased down to 50 ppm (80 ppm) at the opposite side. On the other hand, for the case of the control sample, neither the concentration of toluene nor the concentration of cyclohexane was decreased.

On the other hand, for the case of nonwoven cloth impregnated with a solution containing pectin (USPL 0.5%) and DNA-Na (0.5%), the concentration of toluene (cyclohexane) was decreased down to 40 ppm (50 ppm) at the opposite side.

From the above, it was confirmed that a filter formed of these substances effectively captured toxic substances vaporized and distributed in the air.

Accordingly, it is obvious that the biological preparation of the present invention satisfactorily adsorbs gasification toxic substances for the normal amount of ventilation of the human body.

INDUSTRIAL APPLICABILITY

As has been described above, the biological preparations and contact prevention methods according to the present invention are effective for reducing exposure of a living body to an exogenous disturbing factor, and are particularly suitable for protection against pollen allergic diseases and for preventing the progress of disease conditions.

What is claimed is:

1. A method for inhibiting onset of or treating pollen allergy reactions in a person having pollen allergy comprising administering to said person an effective amount of a preparation, wherein the preparation comprises a uronic acid-containing polysaccharide and a negatively charged macromolecular DNA.

2. The method of claim 1, wherein the preparation is administered as an eye drop.

3. The method of claim 1, wherein the preparation is administered as a gargle.

4. The method of claim 1, wherein the preparation is administered to a nasal membrane.

5. The method of claim 4, wherein the preparation is administered as a nose drop.

6. The method of claim 4, wherein the preparation is administered as a topical cream.

7. The method of claim 4, wherein the preparation is administered as a nose spray.

8. The method of claim 1, wherein the uronic acid-containing polysaccharide is a pectin.

9. The method of claim 1, wherein a concentration of the uronic acid-containing polysaccharide in the preparation is about 0.3 to about 3.0%; and a concentration of the DNA in the preparation is about 0.03 to about 3.0%.

10. The method of claim 1, wherein the preparation comprises an anti-allergic agent.

11. The method of claim 1, wherein the preparation comprises a steroid drug.

12. The method of claim 1, wherein the preparation comprises a component of plant origin.

13. The method of claim 1, wherein the preparation comprises a compound selected from the group consisting of a buffering agent, solubilizing agent, isotonizing agent, stabilizing agent, tackifying agent, chelating agent, pH adjuster, refrigerant agent, antimicrobial agent, and anti-inflammatory agent.

14. A method for inhibiting onset of or treating eye itching or nose itching in a person having pollen allergy, comprising administering to said person an effective amount of a preparation comprising a uronic acid-containing polysaccharide and a negatively charged macromolecular DNA.

15. A method for inhibiting pollen allergens from binding to cell surface acceptors of a person having pollen allergy, comprising administering to said person an effective amount of a preparation, wherein the preparation comprises a uronic acid-containing polysaccharide and a negatively charged macromolecular DNA.

* * * * *